(12) United States Patent
Nomura et al.

(10) Patent No.: US 8,841,236 B2
(45) Date of Patent: Sep. 23, 2014

(54) METHOD FOR IMPARTING STRESS TOLERANCE TO PLANT, PLANT STRESS TOLERANCE IMPARTING COMPOSITION AND USE THEREOF

(75) Inventors: Takayuki Nomura, Wakayama (JP); Masatoshi Kamei, Wakayama (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 13/809,601

(22) PCT Filed: Jul. 16, 2010

(86) PCT No.: PCT/JP2010/062063
§ 371 (c)(1),
(2), (4) Date: Jan. 11, 2013

(87) PCT Pub. No.: WO2012/008042
PCT Pub. Date: Jan. 19, 2012

(65) Prior Publication Data
US 2013/0116121 A1    May 9, 2013

(51) Int. Cl.
*A01N 43/02* (2006.01)
*A01N 43/00* (2006.01)
*A01G 7/06* (2006.01)
*A01N 43/16* (2006.01)

(52) U.S. Cl.
CPC . *A01N 43/16* (2013.01); *A01G 7/06* (2013.01)
USPC ......... 504/140; 504/116.1; 504/118; 504/129

(58) Field of Classification Search
None
See application file for complete search history.

(56) References Cited

U.S. PATENT DOCUMENTS

| 4,673,530 | A | 6/1987 | Hara |
| 2003/0074696 | A1 | 4/2003 | Ohsumi et al. |
| 2009/0270254 | A1 | 10/2009 | Thielert et al. |
| 2010/0107473 | A1 | 5/2010 | Zhang et al. |
| 2011/0100079 | A1 | 5/2011 | Kamei |

FOREIGN PATENT DOCUMENTS

| CN | 1692701 | A | 11/2005 |
| CN | 101646770 | A | 2/2010 |
| JP | 59-219384 | A | 12/1984 |
| JP | 2-104501 | A | 4/1990 |
| JP | 4-20589 | A | 1/1992 |
| JP | 5-260907 | A | 10/1993 |
| JP | 5-306279 | A | 11/1993 |
| JP | 5-339117 | A | 12/1993 |
| JP | 11-71218 | A | 3/1999 |
| JP | 11-269021 | A | 10/1999 |
| JP | 2000-129169 | A | 5/2000 |
| JP | 2002-262885 | A | 9/2002 |
| JP | 2003-113139 | A | 4/2003 |
| JP | 2005-192534 | A | 7/2005 |
| JP | 2006-81971 | A | 3/2006 |
| JP | 2007-217522 | A | 8/2007 |
| JP | 2011-207828 | A | 10/2011 |
| WO | WO 2009/028626 | A1 | 3/2009 |
| WO | WO 2010/122956 | A1 | 10/2010 |

OTHER PUBLICATIONS

"Tanpakushitsu, Kakusan, Kouso (Proteins, Nucleic Acids, Enzymes)" Kyoritsu Shuppan Co., Ltd., vol. 44, No. 15, 1999, pp. 54-65.
International Search Report issued in PCT/JP2010/062063, mailed on Nov. 9, 2010.
Chinese Office Action dated Jun. 3, 2013 for Chinese Application No. 201080067601.4, with English Translation.
Meng, Study on Synthesis and Adsorption Properties of Cellulose Derivatives, Ph.D. Dissertation of Tianjin University, pp. 1-112, Jun. 1, 2005.

*Primary Examiner* — Tracy Vivlemore
*Assistant Examiner* — Monica Shin
(74) *Attorney, Agent, or Firm* — Birch, Stewart, Kolasch & Birch, LLP

(57) ABSTRACT

A method for imparting a stress tolerance to a plant that can provide the plant with such a stress tolerance that enhances growth in an environment where a variety of stresses on the plant occur is provided. The method for imparting a stress tolerance to a plant includes the step of applying, to a plant placed under a stressful cultivation condition that yields a plant stress level of 111 to 200%, a plant stress tolerance imparting composition containing at least one cellulose derivative selected from the group consisting of methyl cellulose (MC), hydroxymethyl cellulose (HMC), ethyl cellulose (EC), hydroxyethyl cellulose (HEC), propyl cellulose (PC), hydroxypropyl cellulose (HPC), hydroxypropyl methyl cellulose (HPMC), hydroxyethyl methyl cellulose (HEMC), hydroxyethyl propyl cellulose (HEPC), methyl ethyl cellulose (MEC), methyl propyl cellulose (MPC) and ethyl propyl cellulose (EPC); catechins; and water, the cellulose derivative being contained in an amount of 45.0 to 99.5 wt % of the total components of the plant stress tolerance imparting composition except water. The present invention also provides the plant stress tolerance imparting composition and use of the plant stress tolerance imparting composition.

4 Claims, No Drawings

METHOD FOR IMPARTING STRESS TOLERANCE TO PLANT, PLANT STRESS TOLERANCE IMPARTING COMPOSITION AND USE THEREOF

TECHNICAL FIELD

The present invention relates to a method for imparting a stress tolerance to a plant, a plant stress tolerance imparting composition, and use of the plant stress tolerance imparting composition.

BACKGROUND ART

About one third of the land on the earth belongs to an arid region, and further expansion of the arid region due to further global warming is expected. Also to address serious food shortages due to population growth, the development of techniques to improve, maintain, and increase plant yields are urgently needed in regions that are arid, accumulate salt, or have a high or low temperature for plants, i.e., regions where in a conventional manner plants are unlikely to grow or growth is hindered and yields are reduced.

When growing plants in a natural or artificial environment, they are subjected to a variety of stresses such as temperature (high temperature, low temperature, freezing), the severity of wind, light intensity (strong light, weak light), dryness, the toxicity of inorganic substances (e.g., salts, heavy metals, and aluminium), lack of oxygen, mechanics (hard soil), and pests. However, plants, unlike animals, cannot migrate to protect themselves from a variety of stresses. It is known that plants therefore produce, when they are subjected to a stress, a variety of substances in their bodies in order to develop stress tolerances, for example, compatible solutes such as proline, glycine betaine, and sugars (Non-patent Document 1). Moreover, it is known that when plants are subjected to such stresses, they produce an aging hormone such as abscisic acid to slow or terminate growth, and as a result yields are reduced.

Methods for enhancing such stress tolerances of plants include a method that involves selection and breeding as well as gene modification (See Patent Document 1) and application of plant energizers such as sugars, organic acids, and amino acids (See Patent Document 2). Further, it is also known that catechins are effective plant growth accelerators (See Patent Documents 3 and 4, for example).

PRIOR ART DOCUMENTS

Patent Documents
Patent Document 1: JP 2002-262885 A
Patent Document 2: JP 2005-192534 A
Patent Document 3: JP H5-339117 A
Patent Document 4: JP 2003-113139 A
Non-Patent Documents
Non-patent Document 1: "Tanpakushitsu, Kakusan, Kouso (Proteins, Nucleic Acids, Enzymes)" (Kyoritsu Shuppan Co., Ltd.), Vol. 44, No. 15, pp. 54 to 65, 1999

DISCLOSURE OF INVENTION

Problem to be Solved by the Invention

However, the methods described in Patent Documents 1 and 2 impart stress tolerances only somewhat, not producing sufficient effects, and none of the methods is currently practically used.

An object of the present invention is to provide a method for imparting a stress tolerance to a plant that can provide the plant with such a stress tolerance that enhances growth in environments where a variety of stresses on the plant occur, a plant stress tolerance imparting composition, and use of the plant stress tolerance imparting composition.

Means for Solving Problem

The method of the present invention is a method for imparting a stress tolerance to a plant. The method includes the step of applying, to a plant placed under a stressful cultivation condition that yields a plant stress level of 111 to 200%, a plant stress tolerance imparting composition containing at least one cellulose derivative selected from the group consisting of methyl cellulose (MC), hydroxymethyl cellulose (HMC), ethyl cellulose (EC), hydroxyethyl cellulose (HEC), propyl cellulose (PC), hydroxypropyl cellulose (HPC), hydroxypropyl methyl cellulose (UPMC), hydroxyethyl methyl cellulose (HEMC), hydroxyethyl propyl cellulose (HEPC), methyl ethyl cellulose (MEC), methyl propyl cellulose (MPC) and ethyl propyl cellulose (EPC); catechins; and water, the cellulose derivative being contained in an amount of 45.0 to 99.5 wt % of the total components of the plant stress tolerance imparting composition except water.

Further, the plant stress tolerance imparting composition of the present invention is a plant stress tolerance imparting composition that contains: at least one cellulose derivative selected from the group consisting of methyl cellulose (MC), hydroxymethyl cellulose (HMO, ethyl cellulose (EC), hydroxyethyl cellulose (HEC), propyl cellulose (PC), hydroxypropyl cellulose (HPC), hydroxypropyl methyl cellulose (HPMC), hydroxyethyl methyl cellulose (HEMC), hydroxyethyl propyl cellulose (HEPC), methyl ethyl cellulose (MEC), methyl propyl cellulose (MPC) and ethyl propyl cellulose (EPC); catechins; and water. The cellulose derivative is contained in an amount of 45.0 to 99.5 wt % of the total components of the plant stress tolerance imparting composition except water.

Further, the method for producing a plant of the present invention includes the method for imparting a stress tolerance to a plant of the present invention.

Further, use of the plant stress tolerance imparting composition of the present invention is for imparting a stress tolerance to a plant placed under a stressful cultivation condition that yields a plant stress level of 111 to 200%.

Effects of the Invention

According to the present invention, a method for imparting a stress tolerance to a plant that can provide the plant with such a stress tolerance that enhances growth in environments where a variety of stresses on the plant occur, a plant stress tolerance imparting composition, and use of the plant stress tolerance imparting composition are provided.

DESCRIPTION OF THE INVENTION

The term "plants" as used herein refer to plants that may be associated with the term itself, such as vegetables, fruits, fruit trees, grains, seeds, bulbs, flowering plants, herbs, and those taxonomically categorized as plants.

When a plant is cultivated in an environment that is different from an environment that is suitable (or close to suitable) for the plant to grow (for example, salt concentration in soil, temperature, humidity, and a like factor can serve as indicators), a phenomenon in which the physiological metabolism of the plant body declines and growth is inhibited occurs. Such a state of a plant is described herein as "a plant is subjected to a stress" or "a plant is stressed".

Generally, for cultivated plants such as agricultural products, cultivation conditions suitable for each plant are known. When a plant is cultivated under such suitable cultivation conditions or conditions similar to such suitable conditions, the plant is not stressed. Herein, whether a plant is stressed or not is determined based on the plant stress level described below. That is, the plant stress level (%) is calculated according to Formula (i) below using the weight of a plant body that has been cultivated under conditions where numerical values indicating salt, dryness, temperature, and the like that can be stressful exceed a suitable range (plant body weight 1: the weight of a plant body that has been cultivated under stress) and the weight of a plant body that has been cultivated under suitable conditions where such a stress factor does not exist (state of not being subjected to a stress) (plant body weight 2: the weight of a plant body that has been cultivated under no stress), and the numerical value of the plant stress level being 111% or more means that the growth is reduced by 10% or more (in terms of weight) and such cultivation conditions are determined as being stressful. As described above, the plant stress tolerance imparting composition of the present invention is applied to a plant placed under a cultivation condition that yields a plant stress level of 111 to 200%. Moreover, the plant stress tolerance imparting composition of the present invention is applied to a plant placed under a stressful cultivation condition that yields a plant stress level of preferably 120 to 180%, and more preferably 120 to 160%. Use of the plant stress tolerance imparting composition on a plant placed under a stressful cultivation condition that yields such a plant stress level produces a more significant effect in terms of imparting a plant stress tolerance. The plant stress level can also be calculated according to Formula (i) using the plant body weights 1 and 2, where the plant body weight 1 is taken as the weight of a plant body that has been cultivated under actual cultivating conditions having specific stress factors and the plant body weight 2 is taken as the weight of a plant body that has been cultivated under conditions simulated in a laboratory or a like facility to eliminate the specific stress factors.

Plant stress level(%)=(Plant body weight 2/Plant body weight 1)×100　(i)

Plant body weight 1: the weight of a plant body that has been cultivated under stress Plant body weight 2: the weight of a plant body that has been cultivated under no stress It is preferable to measure the plant body weight 1 when a stress is reflected as a decrease in the weight after the stress is applied and the growth of a plant is reduced. For example, it is preferable to perform the measurement two weeks after the application of a stress.

Stresses to which a plant is subjected can be classified according to parameters specific to the cultivation conditions. A stress resulting from the salt concentration (measured according to the EC value described below) of a soil or a culture solution may be referred to as a salt stress, a stress resulting from the moisture content (measured according to the pF value described below) of a soil may be referred to as a drying stress, a stress resulting from the temperature of a cultivation environment may be referred to as a temperature stress, a stress resulting from the pH of a soil may be referred to as a pH stress, a stress resulting from the oxygen concentration of a soil may be referred to as an oxygen stress, a stress resulting from physical obstruction may be referred to as an obstruction stress, a stress resulting from a pest may be referred to as a pest stress, a stress resulting from light intensity may be referred to as a light stress, a stress resulting from the firmness of a soil may be referred to as a mechanical stress, a stress resulting from contact may be referred to as a contact stimulus, and so on.

For the plants cultivated in tropical regions, a cultivating environment that does not impose a temperature stress has a temperature higher than 25° C. and lower than 35° C. For the plants cultivated in arid regions, a cultivating environment that does not impose a drying stress has a pF value greater than 2.7 and less than 4.2. If the plants cultivated in the stress-free cultivation environments in tropical and arid regions are cultivated in the later-described stress-free cultivation environments in Japan (temperature higher than 20° C. and lower than 25° C., and a pF value greater than 1.5 and less than 2.7), they will be in the state of being temperature-stressed and drying-stressed.

For the plants cultivated in Japan, a cultivation environment that does not impose any salt stress, drying stress, and temperature stress has an EC value greater than 0.5 S/cm and less than 1.2 mS/cm for soil culture or an EC value greater than 0.6 mS/cm and less than 2.7 mS/cm for hydroponic culture, a pF value greater than 1.5 and less than 2.7, and a temperature higher than 20° C. and lower than 25° C., respectively. It is expected that use of the plant stress tolerance imparting composition of the present invention allows plants cultivated in tropical and arid regions to grow also in the cultivation environment in Japan.

Hereinafter, the effects of the plant stress tolerance imparting composition of the present invention will be described using as examples plants for which the cultivation environment in Japan is a stress-free environment.

The term "plant stress tolerance imparting composition" as used herein refers to a composition that is applied to a plant in a growth environment that imposes a stress on the plant to alleviate the stress on the plant.

The inventors have newly found that a composition, whose principal ingredients are a specific cellulose derivative barely having a plant energizing ability and catechins barely having a stress tolerance imparting ability in an adequate growth environment, imparts a surprising stress tolerance to a plant in the aforementioned environments that impose stresses on the plant. Based on this finding, the inventors have accomplished a method for imparting a stress tolerance to a plant and a plant stress tolerance imparting composition that enable plant growth to be achieved, even under stress, comparably with the growth attained in the adequate growth environment.

The plant stress tolerance imparting composition of the present invention enables plants to favorably grow in a season and a soil that are different from the season and the soil adequate for the plants to grow naturally. Therefore, an industrial benefit, i.e., such plants can be produced throughout the year in any soil regardless of a specific season or soil, can be provided.

That is, the plant stress tolerance imparting composition of the present invention is a plant stress tolerance imparting composition that contains: at least one cellulose derivative selected from the group consisting of methyl cellulose (MC), hydroxymethyl cellulose (HMC), ethyl cellulose (EC), hydroxyethyl cellulose (HEC), propyl cellulose (PC), hydroxypropyl cellulose (HPC), hydroxypropyl methyl cellulose (HPMC), hydroxyethyl methyl cellulose (HEMC), hydroxyethyl propyl cellulose (HEPC), methyl ethyl cellulose (MEC), methyl propyl cellulose (MPC) and ethyl propyl cellulose (EPC); catechins; and water. The cellulose derivative is contained in an amount of 45.0 to 99.5 wt % of the total components of the plant stress tolerance imparting composition except water. Further, in order for the plant stress tolerance imparting composition to express its plant stress tolerance imparting ability properly, the cellulose derivative is contained in an amount of preferably 45.0 to 99.4 wt %, more preferably 45.5 to 99.4 wt %, and still more preferably 46.0 to 99.4 wt % of the total components of the composition except water.

[Cellulose Derivative]

The cellulose derivative used in the present invention is at least one selected from the group consisting of methyl cellulose (MC), hydroxymethyl cellulose (HMC), ethyl cellulose (EC), hydroxyethyl cellulose (HEC), propyl cellulose (PC), hydroxypropyl cellulose (HPC), hydroxypropyl methyl cellulose (HPMC), hydroxyethyl methyl cellulose (HEMC), hydroxyethyl propyl cellulose (HEPC), methyl ethyl cellulose (MEC), methyl propyl cellulose (MPC) and ethyl propyl cellulose (EPC). From the viewpoint of allowing the plant stress tolerance imparting composition to express its plant stress tolerance imparting ability properly, hydroxypropyl cellulose (HPC), hydroxypropyl methyl cellulose (HPMC) or hydroxyethyl cellulose (HEC) is particularly preferable.

The concentration of the cellulose derivative in the plant stress tolerance imparting composition of the present invention, e.g., the concentration when the composition is applied to a plant body by being sprayed onto leaves, is preferably 50 to 50,000 ppm, more preferably 70 to 10,000 ppm, still more preferably 70 to 5,000 ppm, even more preferably 100 to 1,500 ppm, and still even more preferably 100 to 1,000 ppm from the viewpoint of allowing the plant stress tolerance imparting composition to express its plant stress tolerance imparting ability properly. When the composition is applied to an underground portion in soil culture or in hydroponic culture, the concentration is preferably 50 to 50,000 ppm, more preferably 70 to 10,000 ppm, still more preferably 70 to 5,000 ppm, even more preferably 100 to 1,500 ppm, and still even more preferably 100 to 1,000 ppm from the same viewpoint as mentioned above.

[Catechins]

Catechins as used herein is a term used to collectively describe non-epicatechins such as catechin, gallocatechin, catechin gallate, and gallocatechin gallate and epicatechins such as epicatechin, epigallocatechin, epicatechin gallate, and epigallocatechin gallate. Catechins used in the present invention can be extracted from the following tea leaves through water or hot water: green teas such as coarse tea, medium tea, refined tea, powdered tea, and pan-fired tea; half fermented teas collectively referred to as oolong teas such as Iron Goddess, Se Chung, Golden Cassia, and Wuyi rock tea; and fermented teas referred to as black teas such as Darjeeling, Assam and Sri Lanka, all of which are obtained from tea leaves of Camellia plants, e.g., C. sinensis and C. assaimica or hybrids thereof. Further, catechins may be used in the present invention in the form of a solution, for example, a solution obtained by dissolving a tea extract concentrate in a medium or in the form of a mixture of a tea extract and an extracted liquid from tea leaves. The aforementioned tea extract concentrate refers to an extract in the form of a concentrate extracted from tea leaves through hot water or a water-soluble organic solvent, and includes those prepared by the methods whose details are described in, for example, JP S59-219384 A, JP H4-20589 A, JP H5-260907 A and JP H5-306279 A. Examples of commercially available tea extract concentrates include "Polyphenon" manufactured by Mitsui Norin Co., Ltd., "Theaflan" manufactured by ITO EN, Ltd., "Sunphenon" manufactured by Taiyo Kagaku Co., Ltd., and "Sunoolong" manufactured by Suntory Holdings Limited. In addition, catechins may be derived from other raw materials, or may be column-purified and chemically synthesized products. The tea extract concentrate may be in a variety of forms such as a solid, an aqueous solution, and a slurry. Examples of media for dissolving the tea extract concentrate include water, carbonated water and commercially available teas containing catechins.

The concentration of catechins in the plant stress tolerance imparting composition, e.g., the concentration when the composition is applied to a plant body by being sprayed onto leaves, is preferably 0.01 to 5,000 ppm, more preferably 0.1 to 1,000 ppm, still more preferably 1 to 1,000 ppm, even more preferably 8 to 700 ppm, and still even more preferably 9 to 500 ppm from the viewpoint of allowing the plant stress tolerance imparting composition to express its plant stress tolerance imparting ability properly. When the composition is applied to an underground portion in soil culture or in hydroponic culture, the concentration is preferably 0.01 to 5,000 ppm, more preferably 0.1 to 1,000 ppm, still more preferably 1 to 1,000 ppm, even more preferably 8 to 700 ppm, and still even more preferably 9 to 500 ppm from the same viewpoint as mentioned above. Further, in order for the plant stress tolerance imparting composition to express its plant stress tolerance imparting ability properly, catechins are contained in an amount of preferably 0.5 to 55.0 wt %, more preferably 0.8 to 55.0 wt %, still more preferably 0.8 to 54.5 wt %, and even more preferably 1.0 to 54.0 wt % of the total components of the plant stress tolerance imparting composition except water.

Further, from the viewpoint of allowing the plant stress tolerance imparting composition to express its plant stress tolerance imparting ability properly, the ratio between the cellulose derivative and catechins contained in the plant stress tolerance imparting composition (cellulose derivative/catechin) is preferably 0.7 to 500, more preferably 0.8 to 300, still more preferably 0.8 to 200, even more preferably 0.8 to 100, and still even more preferably 0.8 to 80.

[Surfactant]

In order to enhance the wettability of the cellulose derivative over the plant surface, the adhesion of the cellulose derivative to the plant surface, or the permeability of the cellulose derivative through the plant surface, a surfactant can be used in the present invention as needed. Use of a surfactant results in the following. That is, the effect of the cellulose derivative is enhanced or exhibited efficiently, enabling the cellulose derivative to be used in the plant stress tolerance imparting composition of the present invention at a reduced concentration.

Examples of such surfactants include nonionic surfactants, anionic surfactants, carboxylic acid-based surfactants, sulfonic acid-based surfactants, sulfuric acid ester-based surfactants, phosphoric acid ester-based surfactants, and ampholytic surfactants.

Examples of the nonionic surfactants include resin acid esters, polyoxyalkylene resin acid esters, polyoxyalkylene alkyl ethers, polyoxyalkylene alkylphenyl ethers, and alkyl alkanol amides.

Examples of the anionic surfactants include carboxylic acid-based, sulfonic acid-based, sulfuric acid ester-based, and phosphoric acid ester-based surfactants. For the anionic surfactants, at least one surfactant selected from carboxylic acid-based and phosphoric acid ester-based surfactants is preferable from the viewpoint of allowing the plant stress tolerance imparting composition to express its plant stress tolerance imparting ability properly.

Examples of the carboxylic acid-based surfactants include $C_{6-30}$ fatty acids or salts thereof, polyhydric carboxylic acid salts, polyoxyalkylene alkyl ether carboxylic acid salts, polyoxyalkylene alkylamide ether carboxylic acid salts, rosin acid salts, dimer acid salts, polymer acid salts, tall oil fatty acid salts, and esterified modified starch. For the carboxylic acid-based surfactants, esterified modified starch is preferable, and alkenyl-succinated modified starch is more preferable from the viewpoint of allowing the plant stress tolerance imparting composition to express its plant stress tolerance imparting ability properly.

Examples of the sulfonic acid-based surfactants include alkylbenzenesulfonic acid salts, alkylsulfonic acid salts, alkylnaphthalenesulfonic acid salts, naphthalenesulfonic acid salts, diphenyl ether sulfonic acid salts, salts of condensates of alkylnaphthalenesulfonic acid, and salts of condensates of naphthalenesulfonic acid.

Examples of the sulfuric acid ester-based surfactants include salts of alkyl sulfuric acid esters, salts of polyoxyalkylene alky sulfuric acid esters, salts of polyoxyalkylene alkyl phenyl ether sulfuric acids, salts of tristyrenated phenol sulfuric acid esters, and salts of polyoxyalkylene distyrenated phenol sulfuric acid esters.

Examples of the phosphoric acid ester-based surfactants include salts of alkyl phosphoric acid esters, salts of alkylphenyl phosphoric acid esters, salts of polyoxyalkylene alkyl phosphoric acid esters, and salts of polyoxyalkylene alkylphenyl phosphoric acid esters. Examples of salts include ammonium salts, alkanolamine salts, and aliphatic amine salts.

Examples of the ampholytic surfactants include amino acid-based, imidazoline-based, and amine oxide-based surfactants.

Examples of the amino acid-based ampholytic surfactants include acylamino acid salts, acylsarcosine acid salts, acyloyl methylaminopropionic acid salts, alkylaminopropionic acid salts, and acylamidoethylhydroxyethylmethylcarboxylic acid salts.

Examples of the amine oxide-based ampholytic surfactants include alkyldimethylamine oxide, alkyldiethanolamine oxide, and alkylamidepropylamine oxide.

The concentration of surfactant in the plant stress tolerance imparting composition, e.g., the concentration when the composition is applied to a plant body by being sprayed onto leaves, is preferably 0.1 to 10,000 ppm, more preferably 1 to 5,000 ppm, and still more preferably 10 to 1,000 ppm from the viewpoint of allowing the plant stress tolerance imparting composition to express its plant stress tolerance imparting ability properly. When the composition is applied to an underground portion in soil culture or in hydroponic culture, the concentration is preferably 0.01 to 5,000 ppm, more preferably 0.1 to 1,000 ppm, and still more preferably 1 to 500 ppm from the same view point as mentioned above.

Further, from the viewpoint of allowing the plant stress tolerance imparting composition to express its plant stress tolerance imparting ability properly, the surfactant is contained in an amount of preferably 0.1 to 25 wt %, and more preferably 1 to 10 wt % of the total components of the plant stress tolerance imparting composition except water.

[Chelating Agent]

The plant stress tolerance imparting composition of the present invention may further contain a chelating agent. The presence of a chelating agent can dramatically enhance the stability of the plant stress tolerance imparting composition of the present invention that contains an aforementioned cellulose derivative and water, thereby enabling the plant stress tolerance imparting composition to stably produce a stress tolerance imparting effect. Examples of the chelating agent include organic acids that have a chelating ability and salts thereof. Specific examples of the chelating agent include polyhydric carboxylic acids, oxycarboxylic acids, salts of polyhydric carboxylic acids, and salts of oxycarboxylic acids. Examples of the polyhydric carboxylic acids include oxalic acid, malonic acid, succinic acid, fumaric acid, maleic acid, adipic acid, and glutaric acid. Examples of the oxycarboxylic acids include citric acid, gluconic acid, malic acid, heptonic acid, lactic acid, and tartaric acid. Examples of the polyhydric carboxylic acid salts include salts of polyhydric carboxylic acids and alkali metals (such as potassium and sodium), salts of polyhydric carboxylic acids and aliphatic amines. Examples of the oxycarboxylic acid salts include salts of oxycarboxylic acids and alkali metals (such as potassium and sodium), salts of oxycarboxylic acids and alkanolamines, and salts of oxycarboxylic acids and aliphatic amines. These chelating agents may be mixed with inorganic chelating agents. Examples of the inorganic chelating agents include aminocarboxylic acid-based chelating agents such as ethylenediaminetetraacetic acid (EDTA) and salts thereof, nitrilotriacetic acid (NTA) and salts thereof, and 1,2-cydohexanediaminetetraacetic acid monohydrate (CDTA) and salts thereof.

The concentration of the chelating agent in the plant stress tolerance imparting composition, e.g., the concentration when the composition is applied to a plant body by being sprayed onto leaves, is preferably 0.1 to 10,000 ppm, more preferably 1 to 5,000 ppm, and still more preferably 10 to 1,000 ppm from the viewpoint of allowing the plant stress tolerance imparting composition to express its plant stress tolerance imparting ability properly. When the composition is applied to an underground portion in soil culture or in hydroponic culture, the concentration is preferably 0.1 to 10,000 ppm, more preferably 1 to 5,000 ppm, and still more preferably 10 to 1,000 ppm from the same view point as mentioned above.

Further, from the viewpoint of allowing the plant stress tolerance imparting composition to express its plant stress tolerance imparting ability properly, the cheating agent is contained in an amount of preferably 0.1 to 25 wt %, and more preferably 1 to 10 wt % of the total components of the plant stress tolerance imparting composition except water.

[Fertilizer Components]

The plant stress tolerance imparting composition of the present invention may further contain a fertilizer component. Examples of the fertilizer component include organic substances, N, P, K, Ca, Mg, S, B, Fe, Mn, Cu, Zn, Mo, Cl, Si, Na, and the like, as well as inorganic substances and that can be the sources of N, P, K, Ca, and Mg. Examples of such inorganic substances include ammonium nitrate, potassium nitrate, ammonium sulfate, ammonium chloride, ammonium phosphate, sodium nitrate, urea, ammonium carbonate, potassium phosphate, calcium superphosphate, fused magnesium phosphate ($3MgO \cdot CaO \cdot P_2O_5 \cdot 3CaSiO_2$), potassium sulfate, potassium chloride, calcium nitrate, calcium hydroxide, calcium carbonate, magnesium sulfate, magnesium hydroxide, and magnesium carbonate. Examples of the organic substances include poultry manure, cattle manure, bark compost, peptone, amino acid solutions (Mieki), and fermentation extracts. These fertilizer components may be used in conjunction with surfactants. For a cultivation form in which fertilizer components are supplied by irrigation to reduce the excessive application of fertilizers at the time of sowing, such as fertigation or hydroponic culture, it is preferable that the plant stress tolerance imparting composition of the present invention further contains a fertilizer component.

A preferable concentration of fertilizer component in the plant tolerance imparting composition when the composition is applied to a plant body by being sprayed onto leaves is 0.1 to 5,000 ppm for N, P, and K components each, more preferably 1 to 1,000 ppm, and still more preferably 10 to 500 ppm from the viewpoint of allowing the plant stress tolerance imparting composition to express its plant stress tolerance imparting ability properly. When the composition is applied to an underground portion in soil culture or in hydroponic culture, a preferable concentration is 0.1 to 5,000 ppm for N, P, and K components each, more preferably 1 to 1,000 ppm, and still more preferably 10 to 500 ppm from the same viewpoint as mentioned above. Moreover, when the composition contains a plurality of types of fertilizer components, a preferable total concentration of fertilizer component in the case of applying the component by spraying onto leaves is 1 to 10,000 ppm for N, P, and K components combined, more preferably 10 to 5,000 ppm, and still more preferably 50 to 2,000 ppm from the same viewpoint as mentioned above. When the composition contains a plurality of types of fertilizer components, a preferable total concentration of fertilizer component in the case of applying the component to an underground portion in soil culture or in hydroponic culture is 1 to 10,000 ppm for N, P, and K components combined, more preferably 10 to 5,000 ppm, and still more preferably 50 to 2,000 ppm from the same viewpoint as mentioned above.

Further, from the viewpoint of allowing the plant stress tolerance imparting composition to express its plant stress tolerance imparting ability properly, the fertilizer component is contained in an amount of preferably 0.1 to 90 wt %, and more preferably 1 to 50 wt % of the total components of the plant stress tolerance imparting composition except water.

The method for imparting a stress tolerance to a plant of the present invention includes the step of applying the plant stress tolerance imparting composition of the present invention to a plant placed under a stressful cultivation condition that yields a plant stress level of 111 to 200%. In the method, the plant stress tolerance imparting composition may be applied to the portion appearing above the ground (e.g., onto leaves) and/or the portion buried under the ground of the plant but it is preferable to apply the plant stress tolerance imparting composition to the portion appearing above the ground from the viewpoint of imparting a stress tolerance to the plant effectively.

Whether a plant has been provided with a stress tolerance can be determined by calculating the extent of imparting plant stress tolerance (%) according to Formula (ii) below using the weight of a plant body that has been cultivated under stress (without using the plant stress tolerance imparting composition) (plant body weight 1), which weight used in calculating the plant stress level, and the weight of a plant body that has received the plant stress tolerance imparting composition of the present invention through the underground portion or the above-ground portion and that has been cultivated under stress (plant body weight 3). An extent of imparting plant stress tolerance exceeding 100% means that a plant has been provided with a stress tolerance, and it is preferably 105% or greater and more preferably 111% or greater.

Extent of imparting plant stress tolerance(%)=(Plant body weight 3/Plant body weight 1)×100     (ii)

Plant body weight 3: the weight of a plant body that has been cultivated using the plant stress tolerance imparting composition under stress Plant body weight 1: the weight of a plant body that has been cultivated without using the plant stress tolerance imparting composition under stress Use of the plant stress tolerance imparting composition of the present invention can achieve an extent of imparting plant stress tolerance exceeding 110% in the case where a plant is cultivated under cultivation conditions including stress factors such as salt, temperature, and dryness.

In the present invention, a standard extent of imparting plant stress tolerance as measured according to the standard test described below preferably is 111% or greater, and this can be used as a criteria for determining whether a specific compound can impart a stress tolerance or not. During actual cultivation on farm land or in a like place, plants are subjected to a variety of stresses. In the standard test, a stressful environment is specified, and is simulated in a laboratory or a like facility to examine the stress tolerance imparting effect of a test compound. A plant stress tolerance imparting composition that has a standard extent of imparting plant stress tolerance of preferably 111% or greater may be applied to the above-ground portion or the underground portion of a plant. The standard test is described below by taking salt and drying stresses as examples.

[Standard Test]
(I) Plant Preparation

A 50-cell tray is filled with potting soil (fertilizer components: N:P:K=0.4:1.9:0.6 (g)/kg potting soil); and plant seeds are sowed, thinly covered with potting soil, and sufficiently irrigated to allow the seeds to sprout. When the leaves in the 2-leaf stage are fully unfolded, the soil on the plant roots is washed away with running water, and the obtained plant is tested. For the potting soil, Kureha gardening soil manufactured by Kureha Corporation may be used.

(II) Test Condition Setting

The environmental conditions are controlled such that the temperature is 23° C., the relative humidity is 50%, the illuminance is 5000 Lux, and the daily light-dark cycle includes a 16-hour light period and an 8-hour dark period. Such environmental conditions can be attained by, for example, controlling the temperature in a room or a climate chamber where the temperature and the relative humidity can be controlled, and controlling illuminance by a fluorescent light or the like. In a salt stress tolerance imparting test, the plant as prepared above is transplanted in a container (such as a polyethylene container) containing 250 ml of a solution culture medium (in which NaCl is added to tap water so as to give a concentration of 3510 ppm (water potential by NaCl of 0.29 MPa)). In a drying stress tolerance imparting test, the plant as prepared above is transplanted in a container (such as a polyvinyl chloride pot) containing 500 ml of soil for a drying test (to which tap water is added so as to give a pF value of 2.8).

(III-1) Treatment with Plant Stress Tolerance Imparting Composition in Salt Stress Tolerance Imparting Test A test plot, control plot 1, and control plot 2 as described below are prepared. 10 specimens of the plant as prepared above are prepared for each of the test plot, control plot 1, and control plot 2 (30 specimens in total), and they are cultivated hydroponically in each plot for two weeks. Subsequently, the weights of all plant bodies are measured to calculate the average. When preparing an aqueous dispersion, any of the aforementioned surfactants having little effects on the plant may be further included in the aqueous dispersion.

Test plot: 10 ml of an aqueous solution or aqueous dispersion of a test compound (cellulose derivative and catechin) (concentration: 100 ppm) is sprayed onto the leaves of the plant per specimen.

Control plot 1: NaCl is added to the solution culture medium (creating a salt stress; NaCl concentration of 3510 ppm), but no test compound (cellulose derivative and catechin) is given to the plant.

Control plot 2: No NaCl is added to the solution culture medium (creating no salt stress), and no test compound (cellulose derivative and catechin) is given to the plant.

(IV-1) Calculation of Standard Extent of Imparting Plant Salt Stress Tolerance (%) in Salt Stress Tolerance Imparting Test A standard extent of imparting plant salt stress tolerance is calculated as described below using the average of the weights of all plant bodies thus obtained (Formula (ii')).

Standard extent of imparting plant salt stress tolerance (%)=(Plant body weight of test plot/Plant body weight of control plot 1)×100   (ii')

The plant stress level (standard plant salt stress level) attained in the above-described standard test is about 130%. In this regard, the standard plant salt stress level can be calculated according to Formula (i') below.

Standard plant salt stress level(%)=(Plant body weight of control plot 2/Plant body weight of control plot 1)×100   (i')

(III-2) Treatment with Plant Stress Tolerance Imparting Composition in Drying Stress Tolerance Imparting Test A test plot, control plot 1, and control plot 2 as described below are prepared. 10 specimens of the plant as prepared above are prepared for each of the test plot, control plot 1, and control plot 2 (30 specimens in total), and they are cultivated in each plot for two weeks. Subsequently, the weights of all plant bodies are measured to calculate the average. When preparing an aqueous dispersion, any of the aforementioned surfactants having little effects on the plant may be further included in the aqueous dispersion.

Test plot: after planting the plant in soil for a drying test (to which tap water is added so as to give a pF value of 2.8), 10 ml of an aqueous solution or aqueous dispersion of a test compound (cellulose derivative and catechin) (concentration: 100 ppm) is sprayed onto the leaves of the plant per specimen.

Control plot 1: after planting the plant in soil for a drying test (to which tap water is added so as to give a pF value of 2.8), no tap water (creating drying stress) and no test compound (cellulose derivative and catechin) are given to the plant.

Control plot 2: after planting the plant in the soil for a drying test, tap water is given (creating no drying stress) to the plant but no test compound (cellulose derivative and catechin) is given to the plant.

(IV-2) Calculation of Standard Extent of Imparting Plant Drying Stress Tolerance (%) in Drying Stress Tolerance Imparting Test A standard extent of imparting plant drying stress tolerance is calculated as described below using the average of the weights of all plant bodies thus obtained (Formula (ii")).

Standard extent of imparting plant drying stress tolerance(%)=(Plant body weight of test plot/Plant body weight of control plot 1)×100   (ii")

The plant stress level (standard plant drying stress level) attained in the above-described standard test is about 150%. In this regard, the standard plant drying stress level can be calculated according to Formula (i") below.

Standard plant drying stress level(%)=(Plant body weight of control plot 2/Plant body weight of control plot 1)×100   (i")

The aforementioned stressful cultivation condition is preferably a cultivation condition including at least one stress factor in the cultivation environment selected from the group consisting of a salt stress resulting from the salt concentration, a drying stress resulting from the moisture content, and a temperature stress resulting from the temperature.

In soil culture or hydroponic culture, an accumulation of salts that are contained in, for example, fertilizers increases the osmotic pressure of a culture solution and prevents a plant from absorbing water, and as a result a phenomenon in which the growth is inhibited occurs. Such a situation is generally understood that a plant is in a salt-stressed state. Specifically, conditions under which a salt stress is present are where the osmotic potential due to the salts contained in a solution culture medium in hydroponic culture or the osmotic potential due to the salts contained in a soil in soil culture is 0.2 MPa (NaCl concentration of 2,400 ppm) or greater, particularly 0.25 MPa or greater, and more particularly 0.30 MPa or greater. According to the present invention, it is possible to impart a tolerance to a plant so that the plant properly grows under a condition that has such an osmotic potential. The osmotic potential in soil culture is calculated according to Raoult's law presented below once a soil is diluted with water and the molar concentration of the salt ions in the supernatant is analyzed.

Raoult's law: $\Pi(atm)=cRT$ $R=0.082$ (L·atm/mol·K)

$T=$absolute temperature (K)

$c=$molar concentration of ions (mol/L)

1 atm=0.1 MPa

The aforementioned salt stress is a salt stress resulting from, for example, an EC value of 1.2 to 3.4 mS/cm in soil culture or an EC value of 2.7 to 5.0 mS/cm in hydroponic culture. The EC value is an index of salt ion concentration and refers to the reciprocal of the specific resistance of a solution, and the reciprocal of the value of the specific resistance of the solution over a distance of 1 cm is expressed in mS. To obtain an EC value, the electroconductivity of a solution created by diluting an air-dried soil with distilled water in a weight ratio of 1 to 5 in the case of soil culture or the electroconductivity of an undiluted solution in the case of hydroponic culture is measured with a conductance meter.

In soil culture, when the moisture content of a soil declines due to a decrease in the amount of rainfall or the amount of water for irrigation, the amount of water a plant can absorb is reduced, and as a result a phenomenon in which growth is inhibited occurs. Such a situation is generally understood that a plant is in a drying-stressed state. Specifically, a condition includes a drying stress when the pF value of a soil in which a plant is cultivated is no less than 1.7 at which gravitational water cannot be considered as soil moisture, particularly 2.3 or greater, and more particularly 2.5 or greater. According to the present invention, it is possible to impart a tolerance to a plant so that the plant properly grows under a condition that has such a pF value. The condition that includes a drying stress is where the pF value is, for example, 2.7 to 4.2, particularly 2.7 to 4.1, and more particularly 3.0 to 4.1. The pF value can be measured with a soil moisture meter (e.g., the pF meter DIK-8343 manufactured by Daiki Kogyo Co. Ltd.) based on the principles of a pF value measurement method described on pp. 61 and 62 of "Dojyo, Shokubutu Eiyo, Kankyo Jiten (Encyclopedia of Soil, Plant Nutrition, and Environment)" (Matsuzaka et at, Taiyosha Co., Ltd., 1994).

In a cultivation environment, when a plant is exposed to a temperature higher or lower than the optimum growth temperature of the plant, a phenomenon in which the physiological metabolism is reduced and growth is inhibited occurs. Such a situation is generally understood that a plant is in a temperature-stressed state. Specifically, a condition includes a temperature stress when the average cultivation temperature of an environment where a plant is cultivated is 25° C. or higher, particularly 28 to 40° C., more particularly 32 to 40° C., or 20° C. or lower, particularly 5 to 17° C., and more particularly 5 to 15° C. According to the plant stress tolerance imparting composition of the present invention, it is possible to impart a tolerance to a plant so that the plant properly grows under a condition that has such an average cultivation temperature. Here, the average cultivation temperature refers to the average of the cultivation temperatures measured every hour regardless of day and night during the cultivation period (period from seeding to the termination of growth).

Plants to which the present invention can impart a stress tolerance include fruiting vegetables, leaf vegetables, root vegetables, rice plants, cereals, flowering plants, and the like. Examples of the fruiting vegetables include cucumber, pumpkin; watermelon, melon, tomato, eggplant, green pepper, strawberry okra, haricots vert, faba bean, garden pea, green soybean, and corn. Examples of the leaf vegetables include Chinese cabbage, vegetables for pickles, pak choy, cabbage, cauliflower, broccoli, Brussels sprout, onion, Welsh onion, garlic, Japanese shallot, leek, asparagus, lettuce, Boston lettuce, celery, spinach, crown daisy, parsely, Japanese honewort, dropwort, udo (*Aralia rhizome*), mioga (*Zingiber mioga*), butterbur, and Japanese basil. Examples of the root vegetables include radish, turnip, burdock, carrot, potato, taro, sweet potato, yam, ginger, and lotus. Examples of the cereals include wheat, barley, oats, rye, and triticale.

The method for producing a plant of the present invention encompasses the method for imparting a stress tolerance to a plant. Specifically, the method for producing a plant of the present invention includes the step of applying the plant stress tolerance imparting composition of the present invention to a plant placed under a stressful cultivation condition that yields a plant stress level of 111 to 200%. According to such a production method, a plant placed under a stressful condition can be efficiently produced.

EXAMPLES

Example 1

Salt Stress Tolerance Imparting Test (Corn)

[Test Method]
(1) A. Soil Culture
Plants as prepared below were cultivated under the below-described conditions set for each Test No. and under the below-described cultivation conditions. Test No.: Reference (1) (reference example conditions (salt stress-free optimum growth conditions)
Cultivation temperature: 23° C., EC value: 1.0 mS/cm (cultivation with Kureha gardening soil), pF value: 1.7 (capillaries in a saturated state)
Test No.: Tests (1), (2) and (3) (example conditions (salt stress conditions))
Cultivation temperature: 23° C.,
EC value: 1.3 mS/cm (test (1)), 2.0 mS/cm (test (2)), 3.0 mS/cm (test (3))
pF value: 1.7 (capillaries in a saturated state)
(2) B. Hydroponic Culture
Plants as prepared below were cultivated under the below-described conditions set for each Test No. and under the below-described cultivation conditions.
Test No.: Reference (2) (reference example conditions (salt stress-free optimum growth conditions)
Cultivation temperature: 23° C., EC value: 1.3 mS/cm (Otsuka ½A formulation)
Test No.: Tests (4), (5) and (6) (example conditions (salt stress conditions))
Cultivation temperature: 23° C.,
EC value: 2.7 mS/cm (test (4)), 3.9 mS/cm (test (5)), 4.8 mS/cm (test (6))

(3) Cultivation Conditions
Illuminance: 5000 Lux (fluorescent light), light/dark cycle: 16 hours/8 hours, Solution culture medium used: Otsuka ½A formulation (a mixed solution of Otsuka House No. 1 (N:P:K=10:8:27) 7.5 g/10 L and Otsuka House No. 2 (N:P:K:Ca=10:0:0:23) 5 g/10 L, total nitrogen (N component): 130 ppm, phosphoric acid (P component): 60 ppm, potassium (K component): 203 ppm)
Cultivation period: two weeks
(4) Plant preparation: a 50-cell trays was filled with Kureha gardening soil manufactured by Kureha Corporation (fertilizer components: N:P:K=0.4:1.9:0.6 g/kg soil), and plant seeds (corn "Waikiki", wheat "Hokushin") were sowed, thinly covered with Kureha gardening soil, and sufficiently watered to allow the seeds to sprout. When the leaves in the 2-leaf stage fully unfolded, the soil on the roots was carefully washed away with running water, and the plants were tested.
(5) Test Chemicals:
Catechin: reagent (manufactured by Wako Pure Chemical Industries, Ltd.)
Cellulose derivative:
Hydroxypropyl cellulose (1): NISSO HPC-L (manufactured by Nippon Soda Co., Ltd.)
Hydroxypropyl cellulose (2): NISSO HPC-SSL (manufactured by Nippon Soda Co., Ltd.)
Hydroxypropyl cellulose (3): NISSO HPC-SL (manufactured by Nippon Soda Co., Ltd.)
Hydroxypropyl cellulose (4): NISSO HPC-M (manufactured by Nippon Soda Co., Ltd.)
Hydroxypropyl cellulose (5): NISSO HPC-H (manufactured by Nippon Soda Co., Ltd.)
Hydroxypropyl methyl cellulose (1): METOLOSE 60SH-03 (manufactured by Shin-Etsu Chemical Co., Ltd.)
Hydroxypropyl methyl cellulose (2): METOLOSE 60SH-50 (manufactured by Shin-Etsu Chemical Co., Ltd.)
Hydroxypropyl methyl cellulose (3): METOLOSE 60SH-10000 (manufactured by Shin-Etsu Chemical Co., Ltd.)
Hydroxypropyl methyl cellulose (4): METOLOSE 65SH-15000 (manufactured by Shin-Etsu Chemical Co., Ltd.)
Hydroxypropyl methyl cellulose (5): METOLOSE 90SH-15000 (manufactured by Shin-Etsu Chemical Co., Ltd.)
Methyl cellulose (1): METOLOSE SM-04 (manufactured by Shin-Etsu Chemical Co., Ltd.)
Methyl cellulose (2): METOLOSE SM-8000 (manufactured by Shin-Etsu Chemical Co., Ltd.)
Hydroxyethyl methyl cellulose: METOLOSE SEB-4000 (manufactured by Shin-Etsu Chemical Co., Ltd.)
Hydroxyethyl cellulose: HEC Daicel SP-200 (manufactured by Daicel Corporation)
Carboxymethyl cellulose Na: CMC Daicel 1190 (manufactured by Daicel Corporation)
Paraffin: reagent (manufactured by Wako Pure Chemical Industries, Ltd.)
(6) Measurement of Plant Salt Stress Level in Soil Culture Tests
A plant salt stress level was measured as follows.
For soil culture, the environmental conditions in a climatic chamber were controlled so as to have a temperature of 23° C., a relative humidity of 50%, an illuminance by a fluorescent light of 5000 Lux, and a daily light-dark cycle of a 16-hour light period and an 8-hour dark period. 10 species of corn as prepared above were prepared for each test (20 species in total) and were transplanted in size-3 (9 cm) pots each containing soil whose EC value had been adjusted to conform to the condition of each of Tests (1) to (3) and Reference (1). After soil-cultivating the plant for two weeks, the weights of all plant bodies were measured to calculate the average. A plant salt stress level was calculated according to Formula (i-1) below using the plant body weight. The EC value, the pF value, the plant body weight and the plant salt stress level thus obtained in each of Tests (1) to (3) and Reference (1) are presented in Table 1a below Plant salt stress level(%)=(Plant body weight of Reference(1)/Plant body weight of any of Tests (1) to (3))×100    (i-1)

TABLE 1a

|  | With salt stress | | | Without salt stress |
| --- | --- | --- | --- | --- |
|  | Test (1) | Test (2) | Test (3) | Reference (1) |
| EC value (mS/cm) | 1.3 | 2 | 3 | 1 |
| pF value | 1.7 | 1.7 | 1.7 | 1.7 |
| Plant body weight | 7.0 | 6.0 | 4.2 | 8.4 |
| Level of plant salt stress (%) | 120 | 140 | 200 | 100 |

As can be seen from Table 1a, the plant salt stress levels in Tests (1) to (3) and Reference (1) were 120%, 140%, 200%, and 100%, respectively.

(7) A. Soil Culture Test

The environmental conditions in a climatic chamber were controlled so as to have a temperature of 23° C., an illuminance by a fluorescent light of 5000 Lux, and a daily light-dark cycle of a 16-hour light period and an 8-hour dark period. Corn as prepared above was transplanted in size-3 (9 cm) pots each containing soil conforming to the condition of each Test No. During the test period, the EC value was controlled by adding a suitable amount of a 10% NaCl solution once a day so as to attain a specific salt stress value. Plant stress tolerance imparting compositions each containing a specific concentration of the cellulose derivative and the catechin component shown in Table 1 (the remainder was water) were prepared and sprayed onto the leaves. Conditions for each test plot (Test No.) are presented in Table 1. 10 specimens were prepared as a test plant for each test plot and were cultivated for two weeks in each test plot. An extent of imparting plant stress tolerance was determined by calculating the average plant body weight of each specimen two weeks after the beginning of the test and was expressed as a relative value where "100" indicated a result identical to that of the untreated plot of a given EC condition. In addition, a reference example (Reference (1)) was constructed to reflect the stress-free optimum cultivation conditions to investigate the plant energizing ability.

The results thus obtained are presented in Table 1. The results show that, as presented in Table 1, the products of the present invention all exhibited an extremely high growth enhancing effect under salt stress conditions (Tests (1), (2) and (3)) having a high EC value and had a high plant energizing ability while they did not exhibit any growth effect under the stress-free conditions of the reference example (Reference (1)). Moreover, when the products of the present invention and the comparative products (comparative example: example without using the plant stress tolerance imparting composition of the present invention) were compared, it was determined that the plant energizing ability of the products of the present invention was higher in respective salt stress conditions.

(8) Measurement of Plant Salt Stress Level in Hydroponic Culture Tests

A plant salt stress level was measured as follows.

For hydroponic culture, the environmental conditions in a climatic chamber were controlled so as to have a temperature of 23° C., a relative humidity of 50%, an illuminance by a fluorescent light of 5000 Lux, and a daily light-dark cycle of a 16-hour light period and an 8-hour dark period. 10 species of corn as prepared above were prepared for each test (20 species in total) and were transplanted in 250-ml polyethylene bottles each containing a solution culture medium whose EC value had been adjusted to conform to the condition of each of Tests (4) to (6) and Reference (2). Each EC value was achieved by taking a ½ Otsuka A formulation having an EC value of 1.3 as a standard and suitably increasing the fertilizer concentration through proportional counting. After cultivating the plant hydroponically for two weeks, the weights of all plant bodies were measured to calculate the average. A plant salt stress level was calculated according to Formula (i-2) below using the plant body weight. The EC value, the plant body weight and the plant salt stress level thus obtained in each of Tests (4) to (6) and Reference (2) are presented in Table 1b below.

Plant salt stress level(%)=(Plant body weight of Reference(2)/Plant body weight of any of Tests (4) to (6))×100    (i-2)

TABLE 1b

|  | With salt stress | | | Without salt stress |
| --- | --- | --- | --- | --- |
|  | Test (4) | Test (5) | Test (6) | Reference (2) |
| EC value (mS/cm) | 2.7 | 3.9 | 4.8 | 1.3 |
| Plant body weight | 7.0 | 6.0 | 4.2 | 8.4 |
| Level of plant salt stress (%) | 120 | 140 | 200 | 100 |

As can be seen from Table 1b, the plant salt stress levels in Tests (4) to (6) and Reference (2) were 120%, 140%, 200%, and 100%, respectively.

(9) B. Hydroponic Culture

The environmental conditions in a climatic chamber were controlled so as to have a temperature of 23° C., an illuminance by a fluorescent light of 5000 Lux, and a daily light-dark cycle of a 16-hour light period and an 8-hour dark period. Corn as prepared above was planted in 250-ml polyethylene bottles each filled with a solution culture medium having a given EC value. Each EC value was achieved by taking a ½ Otsuka A formulation having an EC value of 1.3 as a standard and suitably increasing the fertilizer concentration through proportional counting. Plant stress tolerance imparting compositions each containing a certain concentration of the cellulose derivative and the catechin component shown in Table 1 (the remainder was water) were prepared and sprayed onto the leaves. Conditions for each test plot (Test No.) are presented in Table 1. 10 specimens were prepared as a test plant for each test plot and were cultivated for two weeks in each test plot. An extent of imparting plant stress tolerance was determined by calculating the average plant body weight of each specimen two weeks after the beginning of the test and was expressed as a relative value where "100" indicated a result identical to that of the untreated plot of a given EC condition. In addition, a reference example (Reference (2)) was constructed to reflect the stress-free optimum cultivation conditions to investigate the plant energizing ability.

The results thus obtained are presented in Table 1. As a result, it was found that, as presented in Table 1, the products of the present invention all exhibited an extremely high growth enhancing effect under salt stress conditions having a high EC value (Tests (4), (5) and (6)) and had a high plant energizing ability while they did not exhibit any growth effect under the stress-free conditions of the reference example (Reference Example (2)). Moreover, when the products of the present invention and the comparative products (comparative example: example without using the plant stress tolerance imparting composition of the present invention) were compared, the plant energizing ability of the products of the present invention was higher in respective salt stress conditions.

TABLE 1

| | Example 1: Salt stress test (corn) | | | | | | | |
|---|---|---|---|---|---|---|---|---|
| | Example | | | Reference Example | Example | | | Reference Example |
| Test No. | Test (1) | Test (2) | Test (3) | Reference (1) | Test (4) | Test (5) | Test (6) | Reference (2) |
| Culture method | Soil culture | | | | Hydroponic culture | | | |
| Cultivation temp. °C | 23 | 23 | 23 | 23 | 23 | 23 | 23 | 23 |
| EC value mS/cm | 1.3 | 2 | 3 | 1 | 2.7 | 3.9 | 4.8 | 1.3 |
| PF value | 1.7 | 1.7 | 1.7 | 1.7 | — | — | — | — |
| Plant salt stress lv. % | 120 | 140 | 200 | 100 | 120 | 140 | 200 | 100 |

| | | Plant stress tolerance imparting composition | | | | | Extent of imparting plant stress tolerance (%) | | | |
|---|---|---|---|---|---|---|---|---|---|---|
| | Test plant | Catechin Component (A) | Concentration of(A) (ppm)*1 | Cellulose derivative (B) | Concentration of(B) (ppm)*1 | Applied portion | Test (1) | Test (2) | Test (3) | Reference (1) |
| Ex | 1 | Catechin | 10 | Hydroxypropyl cellulose (1) | 500 | leaf | 132 | 132 | 122 | 103 |
| | 2 | Catechin | 100 | Hydroxypropyl cellulose (1) | 500 | leaf | 135 | 134 | 125 | 103 |
| | 3 | Catechin | 500 | Hydroxypropyl cellulose (1) | 500 | leaf | 141 | 140 | 130 | 103 |
| | 4 | Catechin | 500 | Hydroxypropyl cellulose (1) | 430 | leaf | 139 | 139 | 127 | 103 |
| | 5 | Catechin | 10 | Hydroxypropyl cellulose (1) | 100 | leaf | 130 | 130 | 120 | 103 |
| | 6 | Catechin | 10 | Hydroxypropyl cellulose (1) | 1000 | leaf | 133 | 132 | 123 | 104 |
| | 7 | Catechin | 10 | Hydroxypropyl cellulose (2) | 500 | leaf | 131 | 132 | 121 | 103 |
| | 8 | Catechin | 10 | Hydroxypropyl cellulose (3) | 500 | leaf | 130 | 130 | 122 | 104 |
| | 9 | Catechin | 10 | Hydroxypropyl cellulose (4) | 500 | leaf | 131 | 130 | 121 | 103 |
| | 10 | Catechin | 10 | Hydroxypropyl cellulose (5) | 500 | leaf | 132 | 131 | 120 | 103 |
| | 11 | Catechin | 10 | Hydroxypropyl methyl cellulose (1) | 500 | leaf | 130 | 131 | 120 | 102 |
| | 12 | Catechin | 10 | Hydroxypropyl methyl cellulose (2) | 500 | leaf | 131 | 131 | 121 | 103 |
| | 13 | Catechin | 10 | Hydroxypropyl methyl cellulose (3) | 500 | leaf | 132 | 130 | 122 | 101 |
| | 14 | Catechin | 10 | Hydroxypropyl methyl cellulose (4) | 500 | leaf | 132 | 130 | 121 | 102 |
| | 15 | Catechin | 10 | Hydroxypropyl methyl cellulose (5) | 500 | leaf | 131 | 131 | 122 | 102 |
| | 16 | Catechin | 10 | Methyl cellulose (1) | 500 | leaf | 130 | 130 | 121 | 101 |
| | 17 | Catechin | 10 | Methyl cellulose (2) | 500 | leaf | 131 | 131 | 122 | 101 |
| | 18 | Catechin | 10 | Ethyl cellulose | 500 | leaf | 131 | 131 | 122 | 102 |
| | 19 | Catechin | 10 | Hydroxyethyl methyl cellulose | 500 | leaf | 130 | 131 | 121 | 101 |
| | 20 | Catechin | 10 | Hydroxy ethyl cellulose | 500 | leaf | 130 | 130 | 120 | 102 |
| Comp. Ex. | 1 | Untreated | — | — | — | — | 100 | 100 | 100 | 100 |
| | 2 | Catechin | 100 | — | 0 | leaf | 119 | 118 | 110 | 102 |
| | 3 | Catechin | 50 | Hydroxypropyl cellulose (1) | 30 | leaf | 117 | 117 | 109 | 103 |
| | 4 | Catechin | 0 | Hydroxypropyl cellulose (1) | 500 | leaf | 110 | 110 | 105 | 100 |
| | 5 | Catechin | 1 | Hydroxypropyl cellulose (1) | 500 | leaf | 110 | 110 | 106 | 101 |
| | 6 | Catechin | 10 | Carboxymethyl cellulose Na | 500 | leaf | 118 | 114 | 104 | 103 |
| | 7 | Catechin | 100 | Carboxymethyl cellulose Na | 500 | leaf | 119 | 117 | 110 | 103 |
| | 8 | Catechin | 500 | Carboxymethyl cellulose Na | 500 | leaf | 120 | 119 | 109 | 103 |
| | 9 | Catechin | 10 | Paraffin | 500 | leaf | 109 | 108 | 106 | 104 |
| | 10 | Catechin | 100 | Paraffin | 500 | leaf | 110 | 109 | 105 | 104 |
| | 11 | Catechin | 500 | Paraffin | 500 | leaf | 114 | 112 | 104 | 102 |

| | | Extent of imparting plant stress tolerance (%) | | | | Content of(B) with respect to total components except water (wt %) (B/B + A) × 100 | (B)/(A) |
|---|---|---|---|---|---|---|---|
| | Test plant | Test (4) | Test (5) | Test (6) | Reference (2) | | |
| Ex | 1 | 133 | 132 | 121 | 102 | 98.0 | 50 |
| | 2 | 136 | 135 | 124 | 106 | 83.3 | 5 |
| | 3 | 142 | 142 | 125 | 105 | 50.0 | 1 |
| | 4 | 141 | 141 | 123 | 103 | 46.2 | 0.86 |
| | 5 | 130 | 130 | 121 | 102 | 90.9 | 10 |
| | 6 | 134 | 134 | 122 | 103 | 99.0 | 100 |
| | 7 | 133 | 132 | 121 | 102 | 98.0 | 50 |
| | 8 | 132 | 133 | 122 | 103 | 98.0 | 50 |
| | 9 | 130 | 131 | 121 | 103 | 98.0 | 50 |
| | 10 | 132 | 130 | 122 | 103 | 98.0 | 50 |
| | 11 | 131 | 130 | 120 | 101 | 98.0 | 50 |

TABLE 1-continued

|      |    |     |     |     |     |       |     |
|------|----|-----|-----|-----|-----|-------|-----|
|      | 12 | 130 | 131 | 121 | 101 | 98.0  | 50  |
|      | 13 | 131 | 133 | 120 | 101 | 98.0  | 50  |
|      | 14 | 131 | 131 | 122 | 101 | 98.0  | 50  |
|      | 15 | 132 | 131 | 121 | 102 | 98.0  | 50  |
|      | 16 | 131 | 130 | 120 | 102 | 98.0  | 50  |
|      | 17 | 131 | 130 | 121 | 101 | 98.0  | 50  |
|      | 18 | 132 | 131 | 121 | 102 | 98.0  | 50  |
|      | 19 | 132 | 132 | 121 | 102 | 98.0  | 50  |
|      | 20 | 130 | 130 | 120 | 101 | 98.0  | 50  |
| Comp. Ex. | 1  | 100 | 100 | 100 | 100 | 0.0   | —   |
|      | 2  | 118 | 116 | 111 | 106 | 0.0   | —   |
|      | 3  | 117 | 116 | 111 | 106 | 37.5  | 0.6 |
|      | 4  | 114 | 112 | 110 | 102 | 100.0 | —   |
|      | 5  | 114 | 113 | 110 | 103 | 99.8  | 500 |
|      | 6  | 110 | 110 | 108 | 105 | 98.0  | 50  |
|      | 7  | 111 | 110 | 106 | 109 | 83.3  | 5   |
|      | 8  | 110 | 110 | 105 | 108 | 50.0  | 1   |
|      | 9  | 111 | 110 | 104 | 102 | 98.0  | 50  |
|      | 10 | 110 | 110 | 105 | 103 | 83.3  | 5   |
|      | 11 | 110 | 110 | 104 | 102 | 50.0  | 1   |

*1Concentration where composition as a whole is 100 wt %

Example 2

Drying Stress Tolerance Imparting Test

[Test Conditions]
(1) A. Soil Culture (Cultivation with Kureha Gardening Soil)
Plants as prepared below were cultivated under the below-described conditions set for each Test No. and under the below-described cultivation conditions.
Test No.: Reference (3) (reference example (dying stress-free optimum growth conditions))
Cultivation temperature: 23° C., EC value: 1.0 mS/cm (cultivation with Kureha gardening soil), pF value: 1.7 (capillaries in a saturated state)
Test No.: Tests (7), (8) and (9) (example conditions (drying stress conditions))
Cultivation temperature: 23° C.,
EC value: 1.0 (cultivation with Kureha gardening soil),
pF values: 2.8 (Test (7)), 3.5 (Test (8)), 4.1 (Test (9))
Other conditions were as in Example 1.
(6) Measurement of Plant Drying Stress Level in Soil Culture Test
A plant drying stress level was measured as follows.
For soil culture, the environmental conditions in a climatic chamber were controlled so as to have a temperature of 23° C., a relative humidity of 50%, an illuminance by a fluorescent light of 5000 Lux, and a daily light-dark cycle of a 16-hour light period and an 8-hour dark period. 10 species of wheat as prepared above were prepared for each test (20 species in total) and were transplanted in size-3 (9 cm) pots each containing 500 ml of soil for a drying test whose pF value had been adjusted to conform to the condition of each of Tests (7) to (9) and Reference (3). During the test period, each pF value was adjusted by adding a proper amount of tap water once a day to attain a specific drying stress value. After soil-cultivating the plant for two weeks, the weights of all plant bodies were measured to calculate the average. A plant drying stress level was calculated according to Formula (i-3) below using the plant body weight. The pF value, the EC value, the plant body weight and the plant drying stress level thus obtained in each of Tests (7) to (9) and Reference (3) are presented in Table 2a below.

Plant drying stress level(%)=(Plant body weight of Reference(3)/Plant body weight of Tests (7) to (9))×100　　　(i-3)

TABLE 2a

|  | With drying stress | | Without drying stress | |
|---|---|---|---|---|
|  | Test (7) | Test (8) | Test (9) | Reference (3) |
| pF value | 2.8 | 3.5 | 4.1 | 1.7 |
| EC (mS/cm) | 1.0 | 1.0 | 1.0 | 1.0 |
| Weight of plant body | 6.5 | 5.6 | 4.2 | 8.4 |
| Level of plant drying stress (%) | 130 | 150 | 200 | 100 |

As can be seen from Table 2a, the plant drying stress levels in Tests (7) to (9) and Reference (3) were 130%, 150%, 200%, and 100%, respectively.

(3) Soil Culture Test
The environmental conditions in a climatic chamber were controlled so as to have a temperature of 23° C., an illuminance by a fluorescent light of 5000 Lux, and a daily light-dark cycle of a 16-hour light period and an 8-hour dark period. Wheat as prepared above was planted in size-3 (9 cm) pots each containing soil conforming to the condition of each Test No. During the test period, each pF value was adjusted by adding a proper amount of tap water once a day to attain a specific drying stress value. Plant stress tolerance imparting compositions each containing a specific concentration of the cellulose derivative and catechin component shown in Table 2 (the remainder was water) were prepared and sprayed onto the leaves. Conditions for each test plot (Test No.) are presented in Table 2. 10 specimens were prepared as a test plant for each test plot and were cultivated for two weeks in each test plot. An extent of imparting plant stress tolerance was determined by calculating the average plant body weight of each specimen two weeks after the beginning of the test and was expressed as a relative value where 100 indicated a result identical to that of the untreated plot of a given pF value condition. In addition, a reference example (Reference (3)) was constructed to reflect the drying stress-free optimum cultivation conditions to investigate the plant energizing ability.

A plant drying stress level was calculated according to Formula (i″) above using the results obtained from control plot 1 having conditions for giving a specific drying stress (Test (7), (8) or (9)) and control plot 2 having conditions free of the specific drying stress (Reference (3)). The plant drying stress levels in Tests (7), (8), and (9) were 130%, 150%, and 200%, respectively.

The results thus obtained are presented in Table 2. The results show that, as presented in Table 2, the products of the present invention all exhibited an extremely high growth enhancing effect under drying stress conditions having a high pF value (Tests (7), (8) and (9)) and had a high plant energizing ability while they did not exhibit any growth effect under the drying stress-free conditions of the reference example (Reference Example (3)). Moreover, when the products of the present invention and the comparative products (Comparative Example: Example without using the plant stress tolerance imparting composition of the present invention) were compared, the plant energizing ability of the products of the present invention was higher in respective drying stress conditions.

TABLE 2

Example 2: Drying stress test (wheat)

| | | Example | | | Ref. Ex. |
|---|---|---|---|---|---|
| | | Test No. | | | |
| | | Test (7) | Test (8) | Test (9) | Reference (3) |
| Culture method | | Soil culture | | | |
| Cultivation temp. C.° | | 23 | 23 | 23 | 23 |
| EC value mS/cm | | 1 | 1 | 1 | 1 |
| PF value | | 2.8 | 3.5 | 4.1 | 1.7 |
| Plant drying stress lv. % | | 130 | 150 | 200 | 100 |

| | Test plant | Catechin component (A) | Concentration of (A) (ppm)*1 | Cellulose derivative (B) | Concentration of (B) (ppm)*1 | Applied portion |
|---|---|---|---|---|---|---|
| Ex | 21 | Catechin component (A) | 10 | Hydroxypropyl cellulose (1) | 500 | leaf |
| | 22 | Catechin component (A) | 10 | Hydroxypropyl cellulose (2) | 500 | leaf |
| | 23 | Catechin component (A) | 10 | Hydroxypropyl cellulose (3) | 500 | leaf |
| | 24 | Catechin component (A) | 10 | Hydroxypropyl cellulose (4) | 500 | leaf |
| | 25 | Catechin component (A) | 10 | Hydroxypropyl cellulose (5) | 500 | leaf |
| | 26 | Catechin component (A) | 10 | Hydroxypropyl methyl cellulose (1) | 500 | leaf |
| | 27 | Catechin component (A) | 10 | Hydroxypropyl methyl cellulose (2) | 500 | leaf |
| | 28 | Catechin component (A) | 10 | Hydroxypropyl methyl cellulose (3) | 500 | leaf |
| | 29 | Catechin component (A) | 10 | Hydroxypropyl methyl cellulose (4) | 500 | leaf |
| | 30 | Catechin component (A) | 10 | Hydroxypropyl methyl cellulose (5) | 500 | leaf |
| | 31 | Catechin component (A) | 10 | Methyl cellulose (1) | 500 | leaf |
| | 32 | Catechin component (A) | 10 | Methyl cellulose (2) | 500 | leaf |
| | 33 | Catechin component (A) | 10 | Ethyl cellulose | 500 | leaf |
| | 34 | Catechin component (A) | 10 | Hydroxyethyl methyl cellulose | 500 | leaf |
| | 35 | Catechin component (A) | 10 | Hydroxyl ethyl cellulose | 500 | leaf |
| Comp. Ex. | 11 | Untreated | — | — | — | — |
| | 12 | Catechin component (A) | 100 | — | 0 | leaf |
| | 13 | Catechin component (A) | 50 | Hydroxypropyl cellulose (1) | 30 | leaf |
| | 14 | Catechin component (A) | 0 | Hydroxypropyl cellulose (1) | 500 | leaf |
| | 15 | Catechin component (A) | 1 | Hydroxypropyl cellulose (1) | 500 | leaf |
| | 16 | Catechin component (A) | 10 | Carboxymethyl cellulose Na | 500 | leaf |
| | 17 | Catechin component (A) | 10 | Paraffin | 500 | leaf |

| | Test plant | Extent of imparting plant stress tolerance (%) | | | | Content of (B) with respect to total components except water (wt %) | |
|---|---|---|---|---|---|---|---|
| | | Test (7) | Test (8) | Test (9) | Reference (3) | (B/B + A) × 100 | (B)/(A) |
| Ex | 21 | 135 | 133 | 124 | 104 | 98.0 | 50 |
| | 22 | 132 | 131 | 121 | 102 | 98.0 | 50 |
| | 23 | 131 | 130 | 122 | 104 | 98.0 | 50 |
| | 24 | 132 | 130 | 120 | 103 | 98.0 | 50 |
| | 25 | 132 | 131 | 121 | 103 | 98.0 | 50 |
| | 26 | 130 | 131 | 120 | 101 | 98.0 | 50 |
| | 27 | 131 | 130 | 122 | 101 | 98.0 | 50 |
| | 28 | 132 | 130 | 121 | 102 | 98.0 | 50 |
| | 29 | 131 | 130 | 120 | 101 | 98.0 | 50 |
| | 30 | 131 | 131 | 121 | 101 | 98.0 | 50 |
| | 31 | 132 | 131 | 120 | 102 | 98.0 | 50 |
| | 32 | 130 | 130 | 121 | 101 | 98.0 | 50 |
| | 33 | 130 | 131 | 121 | 101 | 98.0 | 50 |
| | 34 | 130 | 130 | 121 | 102 | 98.0 | 50 |
| | 35 | 131 | 130 | 120 | 101 | 98.0 | 50 |
| Comp. Ex. | 11 | 100 | 100 | 100 | 100 | 0.0 | — |
| | 12 | 118 | 118 | 109 | 102 | 0.0 | 0 |
| | 13 | 117 | 116 | 108 | 103 | 37.5 | 0.6 |

TABLE 2-continued

| | | | | | | |
|---|---|---|---|---|---|---|
| 14 | 110 | 110 | 105 | 100 | 100.0 | — |
| 15 | 111 | 110 | 106 | 101 | 99.8 | 500 |
| 16 | 117 | 113 | 104 | 103 | 98.0 | 50 |
| 17 | 108 | 108 | 106 | 104 | 98.0 | 50 |

*1Concentration where composition as a whole is 100 wt %

INDUSTRIAL APPLICABILITY

The plant stress tolerance imparting method and the plant stress tolerance imparting composition of the present invention are useful in, for example, agriculture practiced in cold and tropical regions.

The invention claimed is:

1. A method for imparting a stress tolerance to a plant, comprising
the step of applying, to a plant placed under a stressful cultivation condition that yields a plant stress level of 111 to 200%, a plant stress tolerance imparting composition comprising at least one cellulose derivative selected from the group consisting of methyl cellulose (MC), hydroxymethyl cellulose (HMC), ethyl cellulose (EC), hydroxyethyl cellulose (HEC), propyl cellulose (PC), hydroxypropyl cellulose (HPC), hydroxypropyl methyl cellulose (HPMC), hydroxyethyl methyl cellulose (HEMC), hydroxyethyl propyl cellulose (HEPC), methyl ethyl cellulose (MEC), methyl propyl cellulose (MPC) and ethyl propyl cellulose (EPC); catechins; and water, the cellulose derivative being contained in an amount of 45.0 to 99.5 wt % of total components of the plant stress tolerance imparting composition except water.

2. The method for imparting a stress tolerance to a plant according to claim 1, wherein the stressful cultivation condition is a cultivation condition comprising at least one stress factor in a cultivation environment selected from the group consisting of a salt stress resulting from a salt concentration, a drying stress resulting from a moisture content, and a temperature stress resulting from a temperature.

3. The method for imparting a stress tolerance to a plant according to claim 2, wherein the salt stress is a salt stress resulting from an EC value of 1.2 to 3.4 mS/cm in soil culture or an EC value of 2.7 to 5.0 mS/cm in hydroponic culture,
the drying stress is a drying stress resulting from a pF value of 2.7 to 4.2, and
the temperature stress is a temperature stress resulting from an average cultivation temperature of 28 to 40° C. or 5 to 17° C.

4. The method for imparting a stress tolerance to a plant according to claim 1, wherein the plant is at least one selected from the group consisting of fruiting vegetables, leaf vegetables, root vegetables, rice plants, cereals, and flowering plants.

* * * * *